(12) United States Patent
Carrel et al.

(10) Patent No.: US 11,413,396 B2
(45) Date of Patent: Aug. 16, 2022

(54) ASSISTED INJECTION DEVICE FOR SELECTIVELY INJECTING A COMPOSITION CONTAINED IN A MEDICAL CONTAINER

(71) Applicant: Becton Dickinson France, Le Pont de Claix (FR)

(72) Inventors: Franck Carrel, Saint Jean de Vaulx (FR); Julien Gagliano, Grenoble (FR); Frédéric Perot, Saint Paul de Varees (FR)

(73) Assignee: Becton Dickinson France, Le Pont de Claix (FR)

( * ) Notice: Subject to any disclaimer, the term of this patent is extended or adjusted under 35 U.S.C. 154(b) by 172 days.

(21) Appl. No.: 16/632,520

(22) PCT Filed: Jul. 20, 2018

(86) PCT No.: PCT/EP2018/069713
§ 371 (c)(1),
(2) Date: Jan. 20, 2020

(87) PCT Pub. No.: WO2019/016351
PCT Pub. Date: Jan. 24, 2019

(65) Prior Publication Data
US 2020/0188593 A1 Jun. 18, 2020

(30) Foreign Application Priority Data

Jul. 21, 2017 (EP) .................................... 17305983

(51) Int. Cl.
*A61M 5/20* (2006.01)
*A61M 5/315* (2006.01)

(52) U.S. Cl.
CPC ...... *A61M 5/2033* (2013.01); *A61M 5/31501* (2013.01); *A61M 5/3158* (2013.01);
(Continued)

(58) Field of Classification Search
CPC .......... A61M 5/31501; A61M 5/31515; A61M 5/31526; A61M 5/2033; A61M 5/3158;
(Continued)

(56) References Cited

U.S. PATENT DOCUMENTS

| 6,048,336 A | 4/2000 | Gabriel |
| 2016/0067420 A1 | 3/2016 | Higgins et al. |

(Continued)

FOREIGN PATENT DOCUMENTS

| EP | 2570145 A1 | 3/2013 |
| JP | 2001513688 A | 9/2001 |

(Continued)

OTHER PUBLICATIONS

Office of Combination Products in the Office of the Commissioner, Guidance for Industry and FDA Staff, Jun. 2013, U.S. Department of Heath and Human Services, 1-29 (Year: 2013).*

*Primary Examiner* — Nilay J Shah
(74) *Attorney, Agent, or Firm* — The Webb Law Firm (57) ABSTRACT

The present disclosure relates to an assisted injection device for injecting a composition contained in a medical container. The injection device includes a main body adapted to receive a medical container in a fixed position relative to the main body. The main body includes an inner wall provided with a toothed surface. The injection device includes a piston. The piston includes a first part and a second part. The first part includes an inner spring-loaded piston rod, and an outer piston body extending coaxially around the inner spring-loaded piston rod. The second part is arranged between the inner spring-loaded piston rod and the outer piston body, and is provided with a pressing member. The injection device includes an actuator connected to the second part of the piston. The actuator is adapted to selectively (Continued)

move the second part between the proximal first position portion and the distal second position.

10 Claims, 8 Drawing Sheets

(52) U.S. Cl.
CPC ... *A61M 5/31515* (2013.01); *A61M 2005/206* (2013.01); *A61M 2005/208* (2013.01); *A61M 2005/2026* (2013.01)

(58) Field of Classification Search
CPC ........... A61M 2005/31508; A61M 2005/2485; A61M 5/24; A61M 5/31548; A61M 5/31555; A61M 5/3156; A61M 5/31591; A61M 5/31578; A61M 2205/58; A61M 2205/581; A61M 2205/582
See application file for complete search history.

(56) References Cited

U.S. PATENT DOCUMENTS

| | | |
|---|---|---|
| 2016/0317749 A1 | 11/2016 | Jugl et al. |
| 2018/0221586 A1 | 8/2018 | Keitel |

FOREIGN PATENT DOCUMENTS

| | | |
|---|---|---|
| KR | 20130025032 A | 3/2013 |
| WO | 2012031627 A1 | 3/2012 |
| WO | 2017054916 A1 | 4/2017 |

\* cited by examiner

ASSISTED INJECTION DEVICE FOR SELECTIVELY INJECTING A COMPOSITION CONTAINED IN A MEDICAL CONTAINER

CROSS-REFERENCE TO RELATED APPLICATIONS

This application is the United States national phase of International Application No. PCT/EP2018/069713 filed Jul. 20, 2018, and claims priority to European Patent Application No. 17305983.3 filed Jul. 21, 2017, the disclosures of which are hereby incorporated by reference in their entirety.

BACKGROUND OF THE INVENTION

The disclosure relates to an assisted injection device for injecting a composition contained in a medical container. The injection device allows the user to control the injection by selectively allowing or stopping the injection, and makes the injection easier for a user that needs to provide less effort for injecting the composition, especially a composition with a high viscosity, as well as controlling the injection rate while performing the injection.

BACKGROUND ART

Prefilled injection devices are common containers to deliver drugs or vaccines to patients and include syringes, cartridges and autoinjectors or the like. They usually comprise a sealing stopper in gliding engagement into a container, the container being filled with a pharmaceutical composition in order to provide the practitioners with a ready-to-use injection device for patients.

A container has a substantially cylindrical shape, and comprises a proximal end able to be stoppered by a sealing stopper, a distal end wherein the pharmaceutical composition is expelled from the container, and a lateral wall extending between the proximal end and the distal end of the container. In practice, the sealing stopper is aimed at moving, upon the pressure exerted by a piston rod, from a proximal end of the container body towards the distal end of the container body, thereby expelling the drug contained into the container body.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical product thus reducing buying and supply chain costs.

In certain cases, the injection of the composition contained in the container with a manual injection device such as a syringe, can be difficult to carry out, due to the force that needs to be applied onto the piston rod for expelling the composition. This occurs, for example, when the composition has a high viscosity, and/or when the injection is carried out manually by a user that cannot push on the piston rod strongly enough with his fingers. The injection can be a self-injection or can be performed by a user, such as a health care professional, to another person. In the case of healthcare professionals performing repetitive injections of viscous drugs to patients, the repetition of the same gesture requiring to apply a high force onto the piston rod to perform the injection may cause repetitive strain injuries.

Autoinjectors can assist the user in performing an automatic injection of the composition. They usually comprise an injection button the user needs to press in order to start the injection.

The injection carried out with an autoinjector is automatic, which means that once the user has pressed the injection button to move the piston, the injection starts and keeps going until the entirety of the composition is injected.

A consequence is that once the user has triggered the injection by pushing the button, the injection cannot be stopped and restarted again. In particular, carrying out multiple injection sequences of fractions of the pharmaceutical composition while stopping the injection between two consecutive sequences is also not possible.

Moreover, the user cannot change the injection rate (or injection speed) while performing the injection with an autoinjector. In other terms, it is not possible to increase or decrease the injection rate while performing the injection.

This lack of control of the injection can generate pain and anxiety to the user, and may lead the user to be unable to perform the injection correctly.

Moreover, similarly to manual injection devices, autoinjectors can encounter difficulties for injecting a composition with a high viscosity, mainly due to an insufficient force applied to the piston rod by the injection mechanism. Hence, the composition is not expelled from the container, or at most expelled at a very low speed.

SUMMARY

In view of the foregoing, there is a strong need for an injection device for injecting a composition contained in a medical container which allows the user to control the injection, in particular to stop the injection then starting it again. There is also a need for such an injection device that allows for an easier injection of the composition compared to the existing injection devices, in particular when the composition has a high viscosity and/or when the user has a reduced physical strength.

Another aim of the disclosure is also to propose an injection device that allows adjusting the injection rate while performing the injection.

An object of the disclosure is thus to provide an injection device for injecting a composition contained in a medical container that overcomes the drawbacks of the known devices.

Such an improved device allows for assisting the user for carrying out easy injection of the composition contained in the container as well as controlling the injection.

One object of the disclosure is an assisted injection device for injecting a composition contained in a medical container, comprising:
  a main body adapted to receive a medical container in a fixed position relative to the main body, the main body comprising an inner wall provided with a toothed surface,
  a piston comprising:

a first part comprising an inner spring-loaded piston rod, and an outer piston body provided with a locking member, the inner spring-loaded piston rod and the outer piston body being translationally movable inside the main body between a proximal rest position and a distal operative position wherein the inner spring-loaded piston rod engages a stopper of the medical container and pushes the stopper in the medical container, a second part arranged between the inner spring-loaded piston rod and the outer piston body, and provided with an pressing member, the second part being selectively slidable relative to the first part between a proximal first position wherein the pressing member presses radially outwardly the locking member in frictional engagement with the toothed surface, and a distal second position wherein the pressing member is remote from the locking member and allows radial inward movement of the locking member and release of the frictional engagement with the toothed surface, an actuator connected to the second part of the piston, adapted to selectively move the second part between the proximal first position and the distal second position.

According to other optional features of the device of the disclosure:

the outer piston body extends coaxially around the inner spring-loaded piston rod, and is connected to the inner spring-loaded piston rod;

the locking member includes at least one flexible tab and the pressing member includes a flared skirt, and wherein when the second part is in the distal second position, the flexible tabs deflect radially inwardly;

the actuator includes a spring-loaded button mounted on the proximal end of the inner piston rod, the second part being selectively slidable by pushing or releasing the spring-loaded button;

the second part comprises at least two arms accommodated in corresponding recesses of the spring-loaded button;

the second part comprises at least two clipping tabs configured to be inserted by clipping into radial openings provided in the outer piston body for blocking the second part at least distally relative to the outer piston body when said second part is in the distal second position;

the main body comprises an inner body coaxial with the main body, the inner body defining an inner housing inside which the inner spring-loaded piston rod is slidably movable by the spring force of the spring arranged therein, and an outer housing between the inner body and the main body inside which the outer piston body and the second part are movable;

each tooth of the toothed surface flares radially outwardly in a distal direction;

the main body comprises a container holder system configured to receive at least a portion of the medical container and to hold the medical container aligned with the movement direction of the inner piston rod so that when moving from the proximal rest position to the distal operative position, the inner piston rod engages the stopper of the medical container and pushes the stopper in the medical container to inject the composition;

the container holder system comprises:

a slot provided in the outer wall of the main body that leads to a housing configured to receive at least a portion of the medical container and to maintain the medical container in a fixed position aligned with the movement direction of the inner piston rod, a through groove provided in the distal wall of the main body, continuous with the slot and extending in the distal wall from the slot, the groove being configured to guide the medical container inserted via the slot to the housing;

the main body is configured to be held in a user's hand, and the piston includes a proximal end configured to be pushed by the user in a distal direction to accelerate the movement of the inner piston rod to the distal operative position when the actuator is actuated.

In this application, the "distal direction" is to be understood as meaning the direction of injection, with respect to the medical container the device of the disclosure is to be mounted on. The distal direction corresponds to the travel direction of the piston rod during the injection, the medical composition contained initially in the medical container being expelled from the latter. The "proximal direction" is to be understood as meaning the opposite direction to said direction of injection.

BRIEF DESCRIPTION OF THE DRAWINGS

Further features and advantages of the disclosure will become apparent from the detailed description to follow, with reference to the appended drawings, in which.

DETAILED DESCRIPTION

The disclosure proposes an assisted injection device for injecting a composition contained in a medical container.

Prior to the injection, the medical container is filled with the composition intended to be injected, and stoppered with a stopper 34 inserted therein. The stoppered medical container 30 is then mounted on the device, and the injection of the composition can be carried out.

Figure 1:
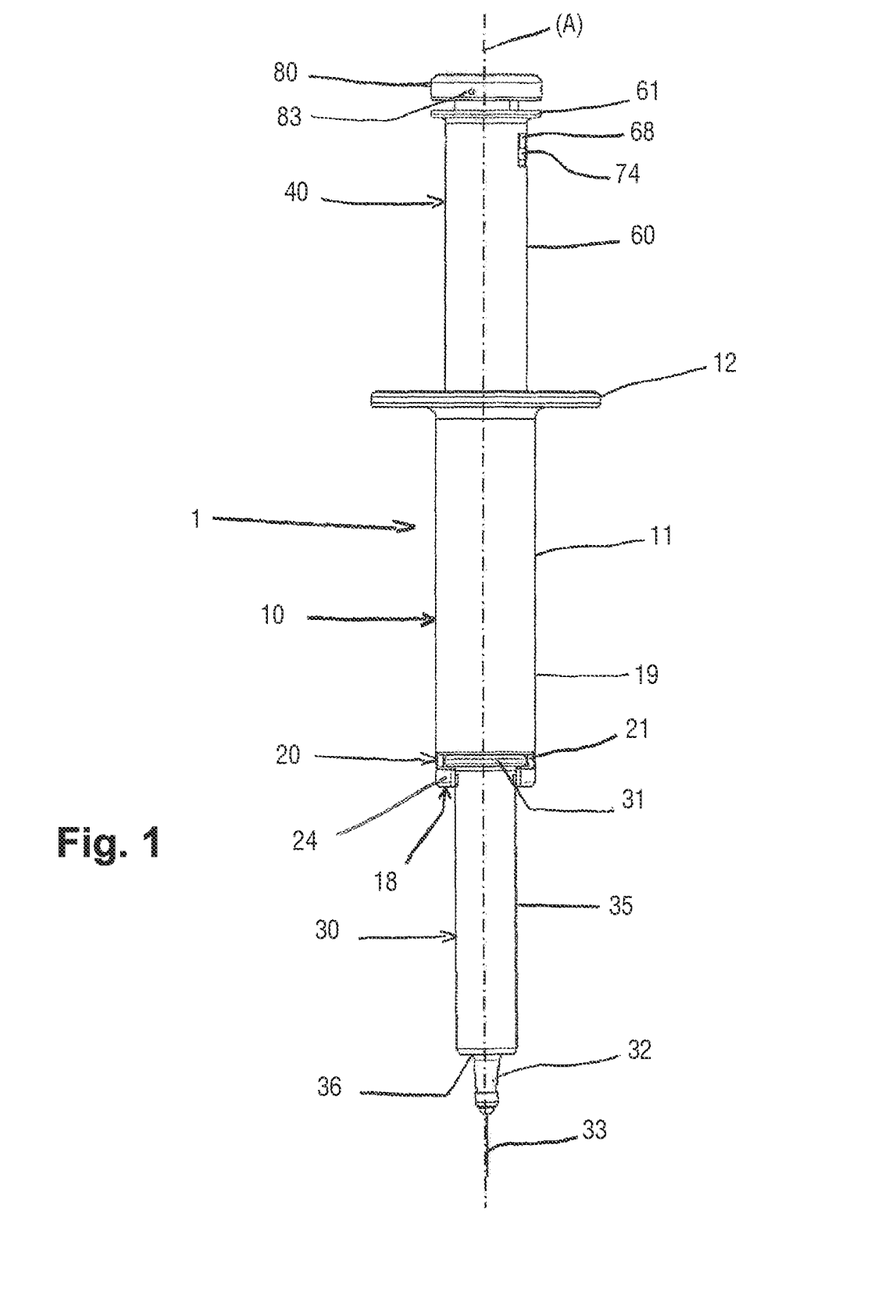
FIG. 1 is a side general view of an embodiment of the injection device of the disclosure.

In reference to FIG. 1, the injection device 1 comprises a main body 10 of a cylindrical shape extending along a longitudinal axis (A). The main body 10 comprises a peripheral wall 19 provided with a grip surface 11 limited proximally by a flange 12 that extends radially outwardly from the axis (A). Hence, when using the device 1, the user can easily grab the main body 10 so that the palm of his hand contacts the grip surface 11 and the upper end of his hand abuts the flange 12, thus facilitating the handling of the device. Or the user can hold the grip surface 11 between his index finger and his middle finger, both abutting the flange 12, as he would normally hold a standard syringe. The device is thus handheld and the dimensions and the weight of the device are advantageously adapted for this purpose.

The medical container 30 comprises a body 35 including a proximal end 31, and a distal end having a tip 32 and a needle 33 extending from thereon. The needle 33 may be covered by a cap (not represented) to prevent any injury when handled before use.

The main body 10 comprises a container holder system 20.

Figure 2:
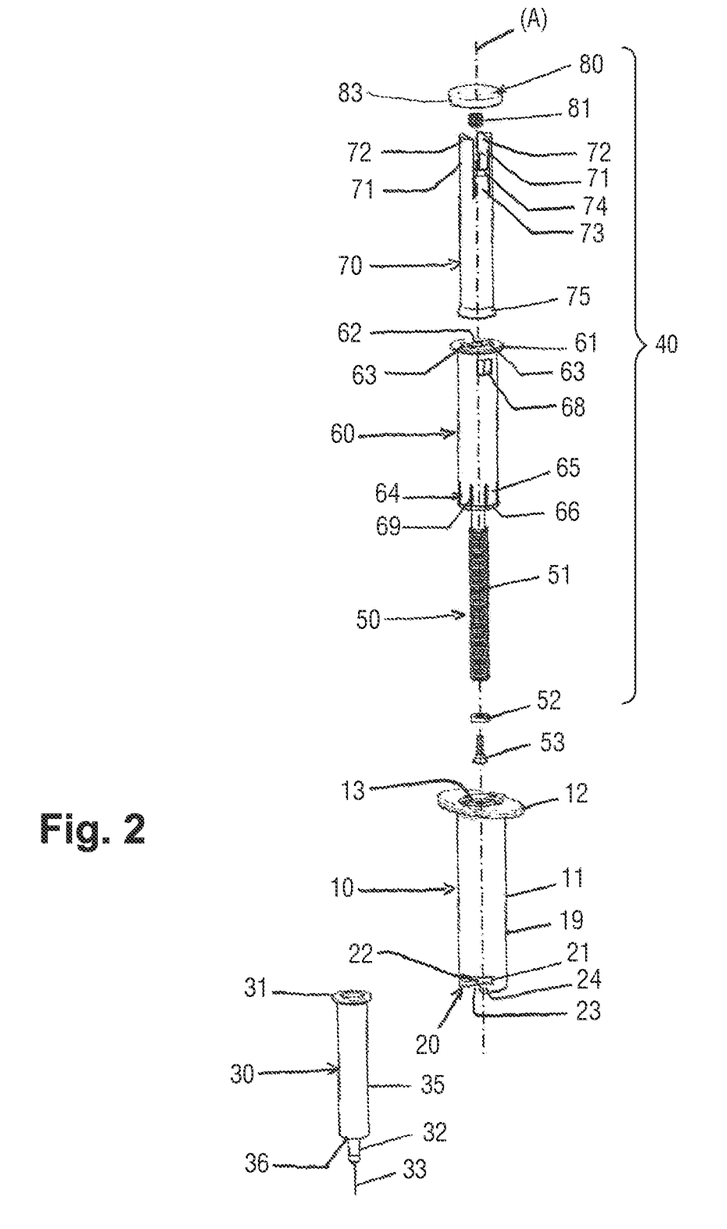
FIG. 2 is an exploded perspective view of the injection device illustrated in FIG. 1.

According to an embodiment illustrated in FIGS. 1 and 2, the container holder system 20 includes a slot 21 provided in the outer wall of the body that leads to a housing 22 adapted to receive the proximal end 31 of the medical container 30.

The container holder system 20 further includes a through groove 23 provided in the distal wall 18 of the main body 10, continuous with the slot 21 and extending in the distal wall of the main body from the slot 21. In a practical way, the proximal end of the container 30 is inserted through the slot 21 and moved in a radial direction along the groove 23 until the container 30 is in a fixed position in the housing 22 relative to the main body 10. The groove 23 separates two projecting parts 24 against which the proximal end 31 of the medical container 30 abuts, thereby preventing the medical container 40 from falling off the device.

To this end, the inner surface of the groove 23 contacts the body of the container 30. In particular, the groove 23 can be configured to prevent the container 30 inserted herein from moving radially, unless the container is moved by a user. The groove is preferably made of a rigid and smooth material, such as rigid plastic or metal (aluminum, stainless steel) for example, for making the insertion of the container therein easier, as well as contributing to maintain the container in a fixed position in the housing 22 during the injection.

The structure of both the slot 21 and the groove 23 may be adapted according to the type of container 30 intended to be stoppered by the device 1.

This embodiment is particularly useful when the medical container 30 is a syringe or the like, as the proximal end 31 of the container 30 is a flange that abuts the projecting parts 24.

Alternatively, when the container 30 is a cylinder or the like (with no proximal flange), the configuration of the container holder system 20 may be adapted accordingly.

Figure 7:
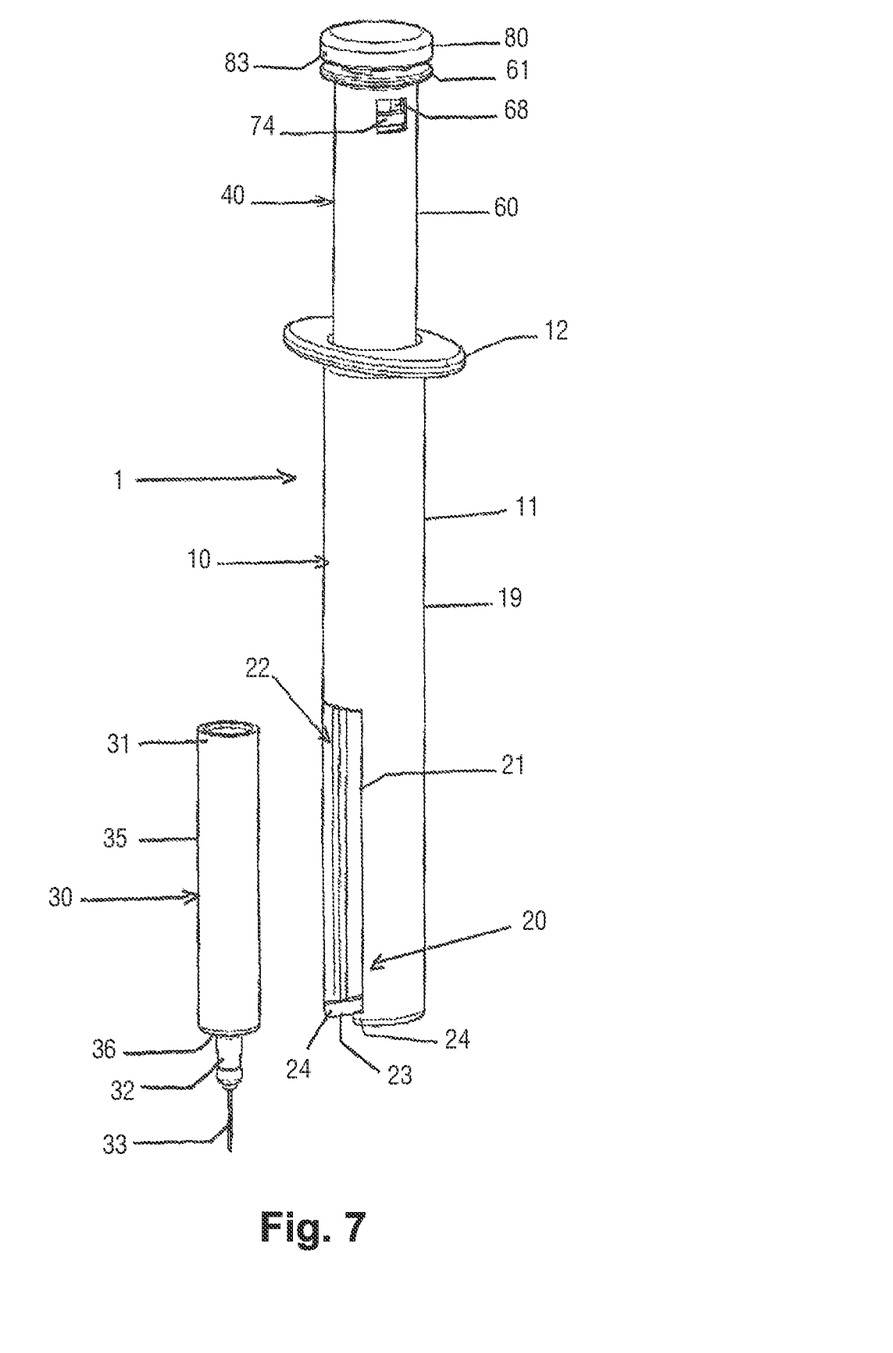
FIG. 7 is a perspective view of the device according to an embodiment of the container holder system.
Figure 8:
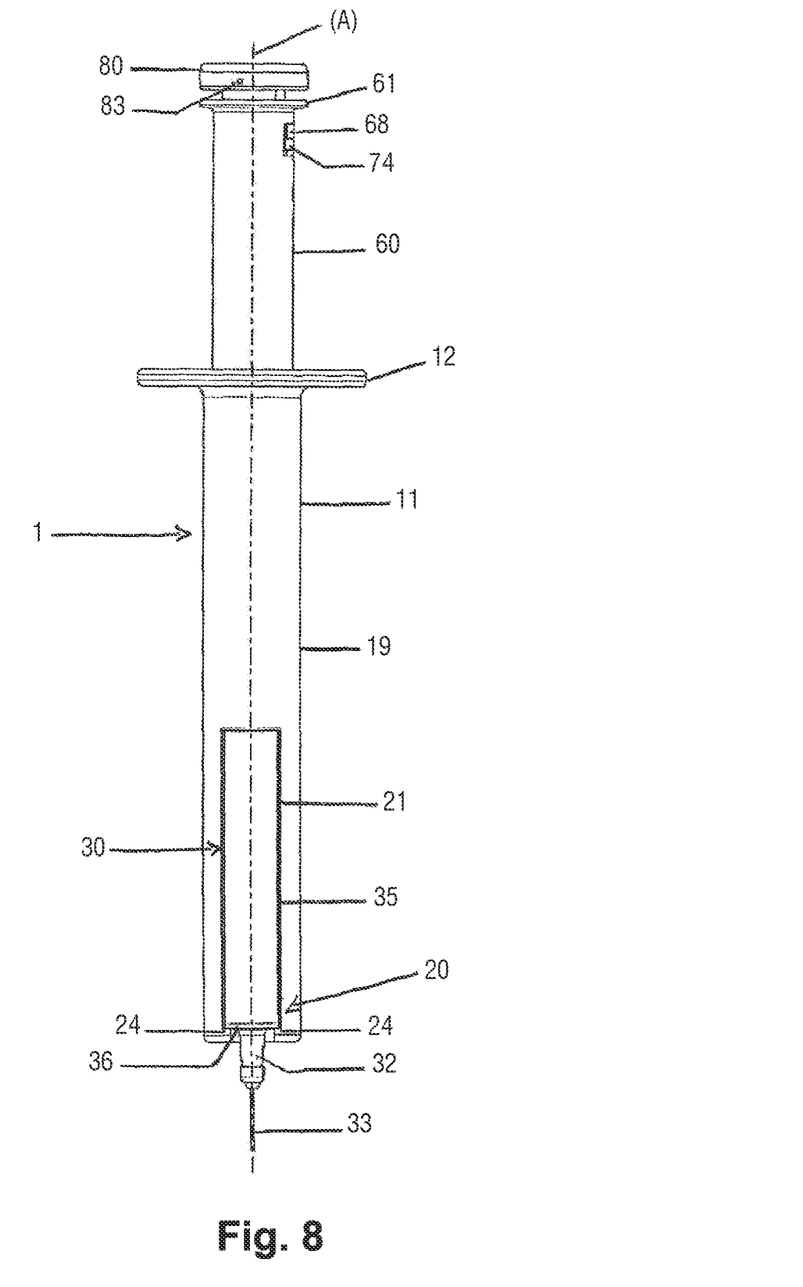
FIG. 8 is a side general view of the device illustrated in FIG. 7, wherein a medical container is inserted in the container holder system.

According to another embodiment illustrated in FIGS. 7 and 8, the dimensions of the slot 21 and the housing 22 are adapted to receive the entire body 35 of the medical container 30 inserted therein, while the tip 32 of the container 30 is moved in a radial direction along the groove 23 until being positioned in the housing 22 where the medical container 30 is maintained in a fixed position relative to the body 10. When the container 30 is positioned in the housing 22, the shoulder 36 (between the body 35 and the tip 32) abuts the projecting parts 24 thereby avoiding the medical container 30 to fall off the device 1. Advantageously, in this situation, only the tip 32 and a needle 33 of the medical container 30 project distally out of the main body 10 of the device. Of course, this embodiment may also be appropriate when the medical container 30 is a syringe or the like, the housing 22 being adapted accordingly to accommodate the flange of the medical container.

Of course, other embodiments of the container holder system are possible without departing from the scope of the disclosure. For example, the medical container 30 could be inserted longitudinally through an opening provided in the distal wall 18 of the body 10, and secured with an insert inserted radially in a slot provided in the peripheral wall 19 of the main body 10.

The device 1 comprises a piston 40 translationally movable inside the main body 10 along the axis (A), and an actuator that preferably includes a spring-loaded button 80 mounted on the proximal end of the piston 40.

Figure 3:
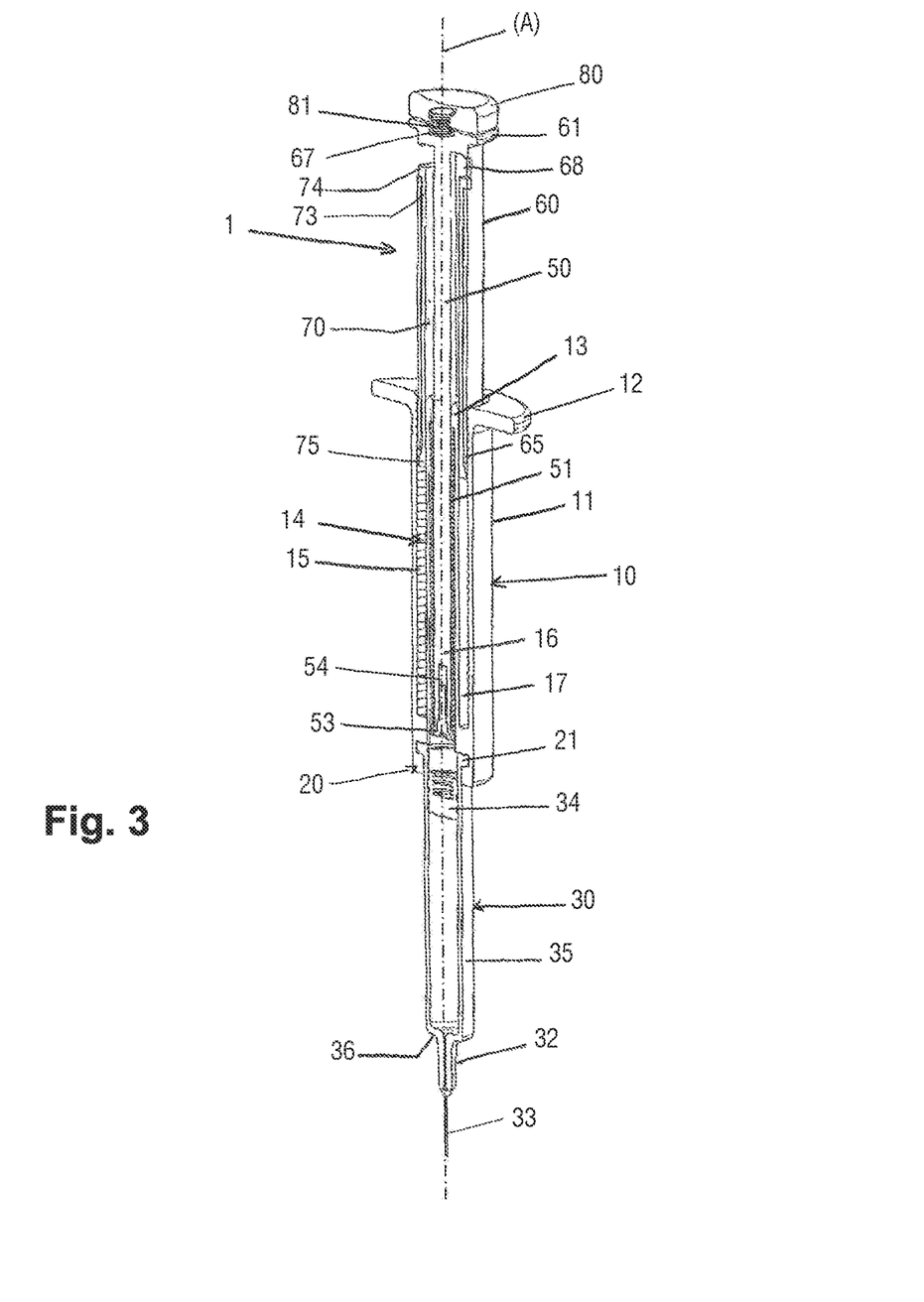
FIG. 3 is a perspective sectional view of the injection device illustrated in FIG. 1.

In reference to FIGS. 2 and 3, the main body 10 is provided with a toothed surface 14 along its inner wall, and includes an inner body 13 extending inside the main body along the axis (A) and fixed relative to the main body. The inner body 13 defines an inner housing 16 and the main body 10 defines with the inner body an outer housing 17 extending in-between.

The piston 40 is in two parts. The first part of the piston comprises an inner piston rod 50 that extends inside the inner body 13 along the axis (A). A spring 51 is arranged inside the inner body 13, coaxially and in contact with the inner piston rod 50. In that way, the inner spring-loaded piston rod 50 is slidable inside the inner body 13 under the force of the spring 51 along the axis (A), between a proximal rest position and a distal operative position wherein the inner piston rod 50 engages the stopper 34 of the medical container 30 and pushes said stopper in the medical container. The proximal end of the spring 51 is fixed to the proximal end of the inner body 13, and the distal end of the spring 51 is secured to the inner piston rod 50 with a ring 52 mounted at the distal end of the inner piston rod and fixed thereon with a screw 53 inserted in a recess 54 provided in the inner piston rod 50. Of course, securing means other than the screw inserted in the recess are usable without departing from the scope of the disclosure.

The first part of the piston 40 further comprises an outer piston body 60 of a cylindrical shape that extends coaxially with and around the inner piston rod 50, at a distance from the inner piston rod. The outer piston body 60 is accommodated in the outer housing 17 thereby extending between the main body 10 and the inner body 13 and facing the toothed surface 14, and is translationally movable in the outer housing 17 along with the inner piston rod 50.

The proximal end of the outer piston body 60 forms a flanged portion 61 that extends radially outwardly from the outer piston body, and is connected to the proximal end of the inner piston rod 50 which extends from thereon. The outer piston body 60 is advantageously in one piece with the inner piston rod 50.

The proximal end of the outer piston body 60 is provided with a stud 62, preferably positioned in a recess 67, coaxial with the inner piston rod 50 and extending proximally from the flanged portion 61. The button 80 is mounted on the stud 62 with a spring 81 arranged around the stud.

Two openings 63 are provided in the proximal end of the outer piston body 60, each forming a passage across said proximal end. The two openings 63 extend radially from the stud 62 and are symmetrical with respect to the stud.

The distal end of the outer piston body 60 is provided with a locking member adapted to extend radially outwardly, namely, away from the axis (A), so as to come into frictional engagement with the toothed surface 14.

According to an embodiment illustrated in FIGS. 1 to 6, the locking member is a skirt 64 comprising a plurality of flexible tabs 65 separated by axial notches 69, adapted to spread radially outwardly so as to come into frictional engagement with the toothed surface 14. To this end, the flexible tabs 65 include hooks 66 with a shape substantially complementary to the shape of the teeth 15 of the toothed surface 14. Moreover, the teeth 15 of the toothed surface 14 preferentially flare radially inwardly in a distal direction, so that the flexible tabs 65 do not abut the flared portion of the teeth 15.

Alternatively, the teeth 15 may flare radially inwardly in a proximal direction. In such case, each tooth is separated from a distally adjacent tooth by an abutment surface onto which a distal end of the flexible tabs 65 may abut. The blocked position of the piston rod 50, relative to the main body, depends on the pitch of the toothed surface 14, which is defined as the distance between two adjacent abutment surfaces. The pitch of the toothed surface may be associated with a unitary dose of composition, so that the user can control the quantity of injected composition by adjusting the number of unitary doses.

The second part 70 of the piston 40 is of a cylindrical shape and extends between the inner piston rod 50 and the outer piston body 60 of the first part, and is slidable therein relative to the first part, and relative to the main body 10.

The proximal end of the second part 70 comprises two diametrically opposed arms 71 configured to be inserted through the openings 63 of the proximal end of the outer piston body 60, into recesses 82 of a shape corresponding to that of the arms 71, provided in the distal surface of the button 80. Radial through holes 72 are provided in the arms 71 and corresponding radial though holes 83 are provided in the button 80, aligned with the diameter of the button and with the holes 72 of the arms. A pin (not represented) is inserted through the holes 72 of the arms and the holes 83 of the button so as to fix the button 80 to the arms 71.

The proximal end of the second part 70 further comprises two diametrically opposed clipping tabs 73 arranged between the arms 71. The clipping tabs 73 are flexible and include a protrusion 74 at their proximal end configured to be inserted by clipping into diametrically opposed radial openings 68 provided in the outer piston body 60, so that the protrusion 74 can abut the distal part of the radial opening 68, thereby blocking the second part 70 distally relative to the outer piston body 60. Moreover, the protrusions advantageously abut the lateral parts of the radial openings 68, causing the second part 70 to be fixed in rotation relative to the outer piston body 60.

The distal end of the second part 70 is provided with a pressing member 75 configured to press radially outwardly the locking member 65, of the outer piston body 60 in frictional engagement with the toothed surface 14 of the main body 10. According to an embodiment illustrated in FIGS. 1 to 6, the pressing member is a unitary flared skirt 75 that flares in a distal direction, and configured to press radially outwardly the locking member which is formed of the flexible tabs 65.

By selectively pushing or releasing the button 80 (actuating or releasing the actuator), the user can start or stop the injection of the composition contained in the medical container 30.

In the following, the functioning of the device will be detailed in reference to the embodiment of the device described above wherein the locking member includes flexible tabs 65 and the pressing member includes a flared skirt 75. It has to be known that other embodiments of the locking member and pressing member would result in a similar functioning, notwithstanding their structural differences.

Figure 4:
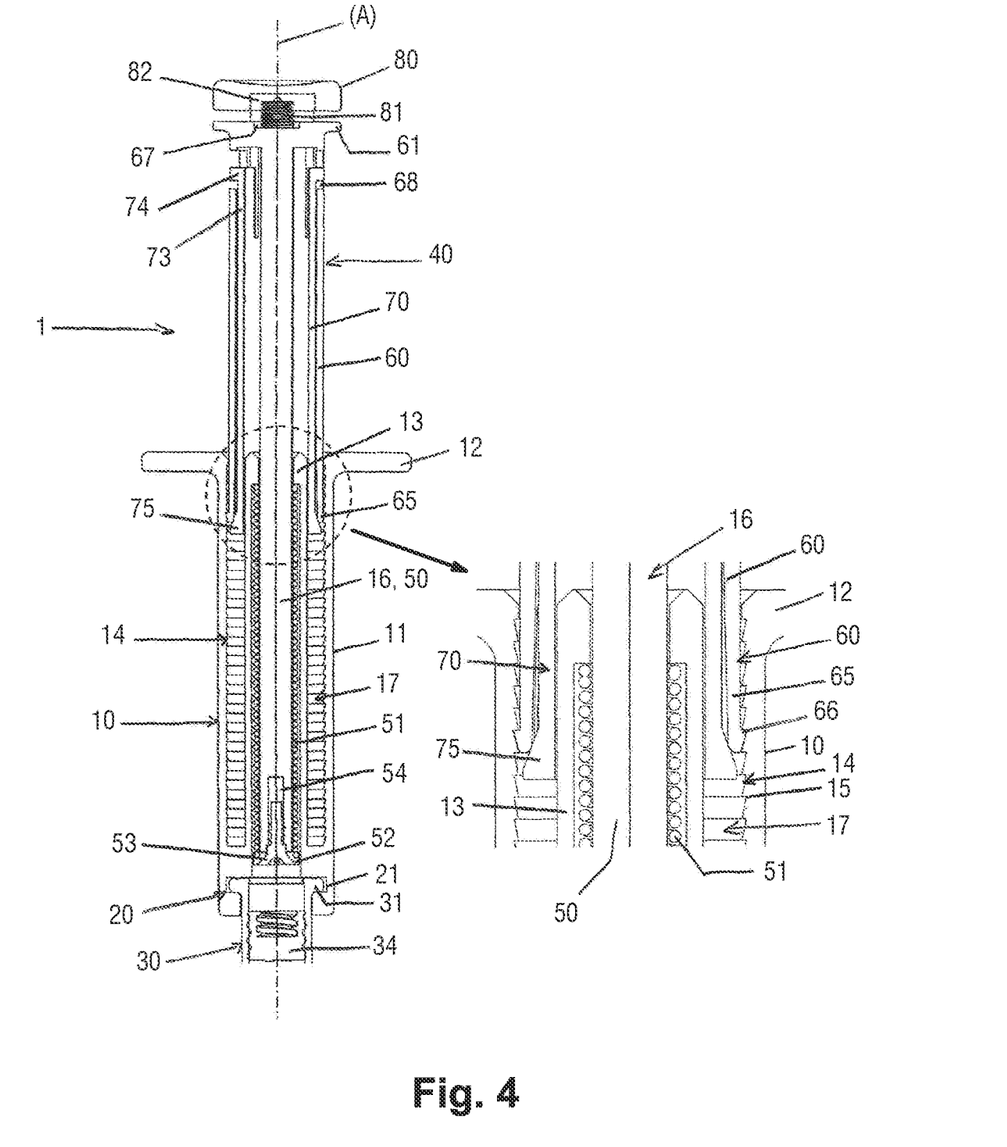
FIG. 4 is a side sectional view of the device, wherein the blocking system blocks the piston rod in a proximal rest position, along with a close-up view of the flexible tabs of the outer piston body and the flared skirt of the intermediate piston body.

As illustrated in FIG. 4, when the button 80 is released, the second part 70 of the piston 40 is in the proximal first position. The inner piston rod 50 and the outer piston body 60 are in a proximal rest position, and the spring 51 of the inner piston rod 50 is compressed.

The protrusions 74 of the clipping tabs 73 are in a determined position in the radial openings 68 of the outer piston body 60, or may abut the proximal part of said radial openings 68.

The flared skirt 75 presses radially outwardly the flexible tabs 65 in frictional engagement with the toothed surface 14, thereby blocking the first part of the piston. The brake force resulting from this frictional engagement opposes the force of the spring 51 of the inner piston rod 50. This brake force depends on the spring force of the button spring 81, the inclination of the slope of the flared skirt 75, and the surface properties and slopes of the flexible tabs 65 and the teeth 15 of the toothed surface 14. Hence, these features may be adjusted so that the brake force is greater than the force of the spring 51 of the inner piston rod 50, for blocking the piston 40 as firmly as possible.

Figure 5:
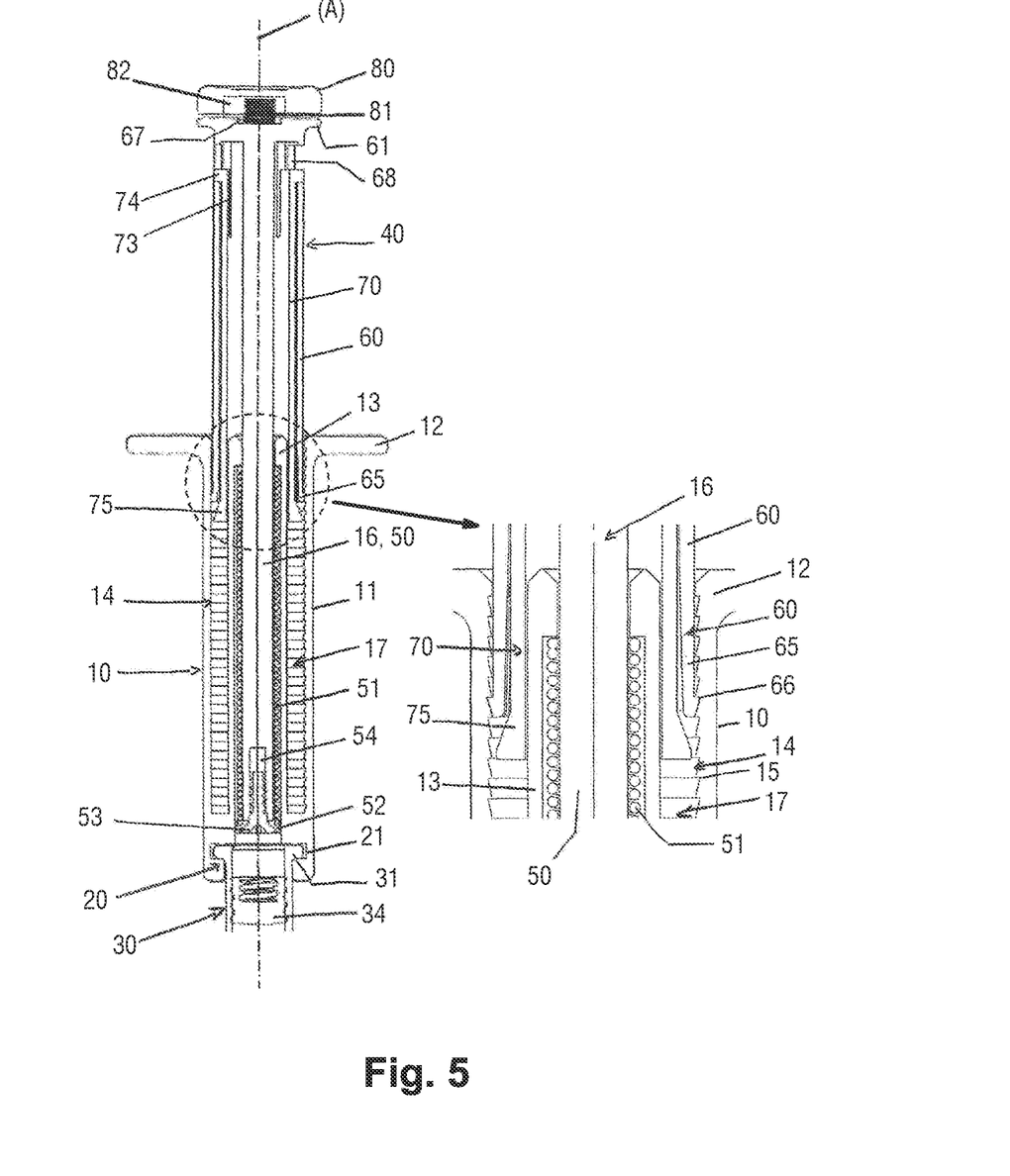
FIG. 5 is a side sectional view of the device, wherein the blocking system is released and the piston rod moved in an operative position, along with a close-up view of the flexible tabs of the outer piston body and the flared skirt of the intermediate piston body.

As illustrated in FIG. 5, when the user pushes the button 80 in a distal direction, the button 80 pushes the arms 71 of the second part 70 of the piston in a distal direction and the protrusions 74 of the clipping tabs 73 abut the distal part of the radial openings 68. The second part 70 of the piston slides in a distal direction relative to the inner piston rod 50 and the outer piston body 60, from the proximal rest position to a distal second operative position wherein the flared skirt 75 is remote from the flexible tabs 65. The flexible tabs 65 deflect radially and inwardly, and disengage the toothed surface 14, thereby releasing the frictional engagement with the toothed surface 14.

The deflection of the flexible tabs 65 causes the first part of the piston to move in a distal direction relative to the main body 10.

The inner piston rod 50 slides in a distal direction along the inner body 13 with the spring force of the spring 51, to a distal operative position wherein the inner piston rod 50 engages the stopper 34 and pushes said stopper in the medical container 30. The composition is thus expelled from the medical container. In this position, the spring 51 of the inner piston rod 50 is at least partially released.

The outer piston body 60 moves translationally in a distal direction along with the inner piston rod 50.

As long as the user keeps pushing the button 80, the flexible tabs 65 remain in a deflected position, radially away from the toothed surface 14. The two parts of the piston keep moving together, assisted by the release of the spring 51 of the inner piston rod 50, and the injection continues.

When the user releases the button 80, the second part 70 of the piston slides back proximally in the proximal rest position and the protrusions 74 of the clipping tabs 73 disengage the proximal part of the radial openings 68. The flexible tabs 65 move back radially outwardly in frictional engagement with the toothed surface 14, thereby blocking the first part of the piston, and the device returns in the situation described previously, the first and second parts of the piston 40 being in a more distal position relative to the main body 10 than previously.

As such, the user can start or stop the injection simply by pressing the button 80 during a certain amount of time or releasing it.

For performing the injection, the user can grip the grip surface 11 with the palm of his hand and push the spring-loaded button 80 with the thumb. Otherwise, the user can hold the grip surface 11 between his index finger and his middle finger, both abutting the flange 12, like he would normally hold a standard syringe.

Moreover, while performing the injection, the user can push the button 80 even harder after the flexible tabs 65 disengage the toothed surface 14. In this case, the force applied to the inner piston rod 50 is a combination of the spring force of the inner piston rod 50 and the force exerted by the user. The movement of the inner piston rod 50 can thus be accelerated, and the injection rate is thus increased. If the user reduces its strength back to the situation wherein the flexible tabs 65 just disengaged the toothed rack, the inner piston rod 50 becomes again driven by the spring 51 only.

Figure 6:
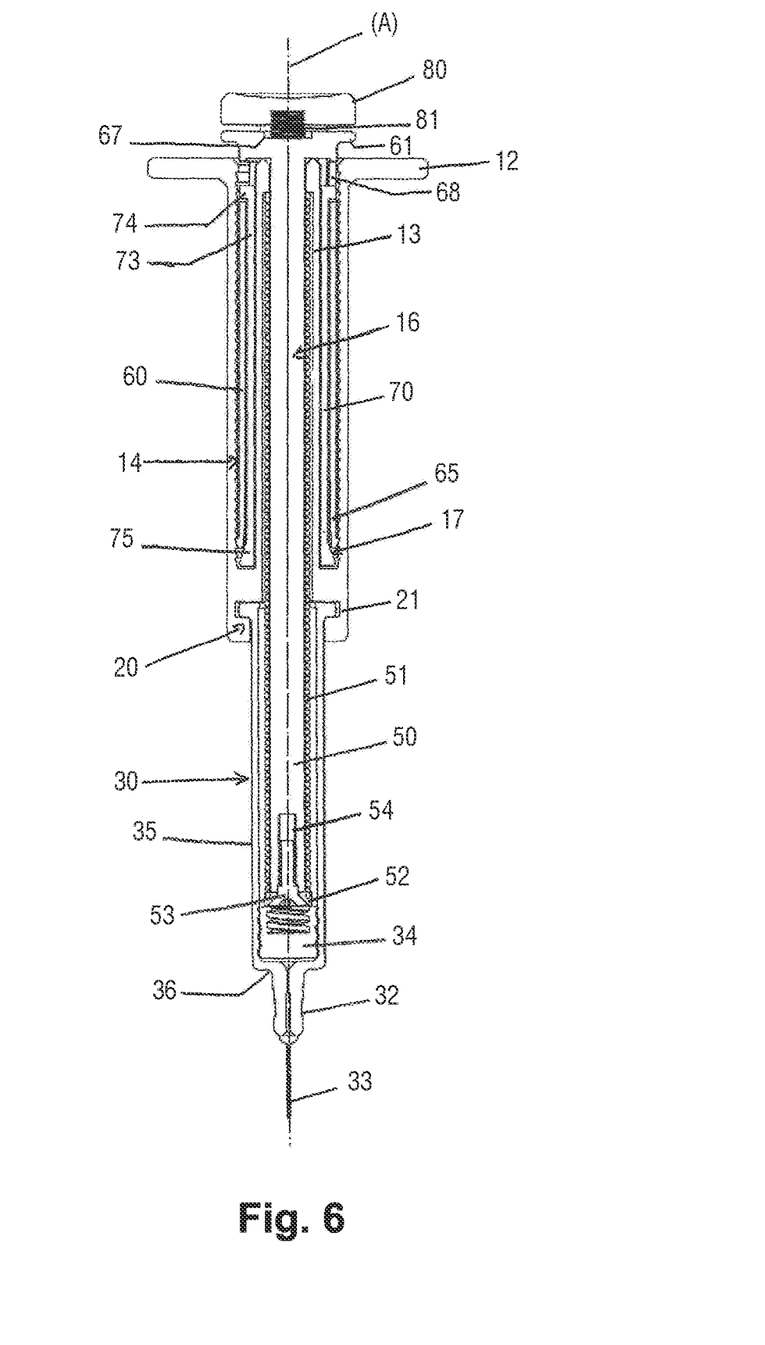
FIG. 6 is a side sectional view of the device at the end of the injection.

In reference to FIG. 6, at the end of the injection, the entirety of the composition has been injected. The stopper 34 abuts the distal end of the medical container 30 and the inner piston rod 50 cannot move further distally. The spring 51 of the inner piston rod 50 is in an at least partially relaxed state.

The proximal end of the outer piston body 60 abuts the proximal end of the inner body 13, and the flared skirt 75 abuts the distal end of the main body 10 and cannot move further distally.

At the end of the injection, the device may be reset manually by the user so as to proceed to another injection. To do so, the piston 40 is pulled by the user in a proximal direction back to the proximal rest position, by grabbing the flanged portion 61 while pushing the button 80. Then the button 80 is released, the empty medical container 30 is removed from the container holder system 20, and a new filled medical container 30 may be positioned in the container holder system 20.

The invention claimed is:

1. An assisted injection device for injecting a composition contained in a medical container, comprising:
   a main body adapted to receive and maintain the medical container in a fixed position relative to the main body, the main body comprising an inner wall provided with a toothed surface;
   a piston comprising:
      a first part comprising an inner spring-loaded piston rod, and an outer piston body extending coaxially around the inner spring-loaded piston rod, the outer piston body being connected to the inner spring-loaded piston rod and provided with at least one lock member, the inner spring-loaded piston rod and the outer piston body being translationally movable inside the main body between a proximal rest position and a distal operative position wherein the inner spring-loaded piston rod engages a stopper of the medical container and pushes the stopper in the medical container, and
      a second part arranged between the inner spring-loaded piston rod and the outer piston body, and provided with a press member, the second part being selectively slidable, relative to the first part, between a proximal first position wherein the press member presses radially outwardly the at least one lock member in frictional engagement with the toothed surface, and a distal second position wherein the press member is remote from the at least one lock member and allows radial inward movement of the at least one lock member and release of the frictional engagement with the toothed surface; and
   an actuator connected to the second part of the piston, adapted to selectively move the second part between the proximal first position and the distal second position.

2. The assisted injection device according to claim 1, wherein the at least one lock member includes at least one flexible tab and the press member includes a flared skirt, and wherein when the second part is in the distal second position, the at least one flexible tab deflects radially inwardly.

3. The assisted injection device according to claim 1, wherein the actuator includes a spring-loaded button mounted on a proximal end of the inner spring-loaded piston rod, the second part being selectively slidable by pushing or releasing the spring-loaded button.

4. The assisted injection device according to claim 3, wherein the second part comprises at least two arms accommodated in corresponding recesses of the spring-loaded button.

5. The assisted injection device according to claim 1, wherein the main body comprises an inner body coaxial with the main body, the inner body defining an inner housing inside which the inner spring-loaded piston rod is slidably movable by the spring force of the spring arranged therein, and an outer housing between the inner body and the main body inside which the outer piston body and the second part are movable.

6. The assisted injection device according to claim 1, wherein the main body comprises a container holder system configured to receive at least a portion of the medical container and to hold the medical container aligned with a movement direction of the inner spring-loaded piston rod so that when moving from the proximal rest position to the distal operative position, the inner spring-loaded piston rod engages the stopper of the medical container and pushes the stopper in the medical container to inject the composition.

7. The assisted injection device according to claim 6, wherein the container holder system comprises:
   a slot provided in an outer wall of the main body that leads to a housing configured to receive at least the portion of the medical container and to maintain the medical container in a fixed position aligned with the movement direction of the inner spring-loaded piston rod, and
   a through groove provided in a distal wall of the main body, continuous with the slot and extending in the distal wall from the slot, the groove being configured to guide the medical container inserted via the slot to the housing.

8. The assisted injection device according to claim 1, wherein the main body is configured to be held in a user's hand, and the piston includes a proximal end configured to be pushed by the user in a distal direction to accelerate the movement of the inner spring-loaded piston rod to the distal operative position when the actuator is actuated.

9. An assisted injection device for injecting a composition contained in a medical container, comprising:
   a main body adapted to receive the medical container in a fixed position relative to the main body, the main body comprising an inner wall provided with a toothed surface;
   a piston comprising:
      a first part comprising an inner spring-loaded piston rod, and an outer piston body extending coaxially around the inner spring-loaded piston rod, the outer piston body being connected to the inner spring-loaded piston rod and provided with at least one lock member, the inner spring-loaded piston rod and the outer piston body being translationally movable inside the main body between a proximal rest position and a distal operative position wherein the inner spring-loaded piston rod engages a stopper of the medical container and pushes the stopper in the medical container, and a second part arranged between the inner spring-loaded piston rod and the outer piston body, and provided with a press member, the second part being selectively slidable, relative to the first part, between a proximal first position wherein the press member presses radially outwardly the at least one lock member in frictional engagement with the toothed surface, and a distal second position wherein the press member is remote from the at least one lock member and allows radial inward movement of the at least one lock member and release of the frictional engagement with the toothed surface, wherein the second part comprises at least two clipping tabs configured to be inserted by clipping into radial openings provided in the outer piston body for blocking the second part at least distally relative to the outer piston body when said second part is in the distal second position; and an actuator connected to the second part of the piston, adapted to selectively move the second part between the proximal first position and the distal second position.

10. An assisted injection device for injecting a composition contained in a medical container, comprising:

a main body adapted to receive a medical container in a fixed position relative to the main body, the main body comprising an inner wall provided with a toothed surface, wherein each tooth of the toothed surface flares radially outwardly in a distal direction;

a piston comprising:

a first part comprising an inner spring-loaded piston rod, and an outer piston body extending coaxially around the inner spring-loaded piston rod, the outer piston body being connected to the inner spring-loaded piston rod and provided with at least one lock member, the inner spring-loaded piston rod and the outer piston body being translationally movable inside the main body between a proximal rest position and a distal operative position wherein the inner spring-loaded piston rod engages a stopper of the medical container and pushes the stopper in the medical container, and a second part arranged between the inner spring-loaded piston rod and the outer piston body, and provided with a press member, the second part being selectively slidable, relative to the first part, between a proximal first position wherein the press member presses radially outwardly the at least one lock member in frictional engagement with the toothed surface, and a distal second position wherein the press member is remote from the at least one lock member and allows radial inward movement of the at least one lock member and release of the frictional engagement with the toothed surface; and an actuator connected to the second part of the piston, adapted to selectively move the second part between the proximal first position and the distal second position.

\* \* \* \* \*